(12) United States Patent
Peng et al.

(10) Patent No.: US 12,336,863 B2
(45) Date of Patent: Jun. 24, 2025

(54) EAR CANAL CLAMP FOR SMALL ANIMALS

(71) Applicant: TAIPEI MEDICAL UNIVERSITY, Taipei (TW)

(72) Inventors: Chih-Wei Peng, Taipei (TW); Chun-Wei Wu, Taipei (TW); Chun-Ying Cai, Taipei (TW); Yen Cheng, Taipei (TW)

(73) Assignee: LEGO STONE CO., LTD., Taichung (TW)

( * ) Notice: Subject to any disclaimer, the term of this patent is extended or adjusted under 35 U.S.C. 154(b) by 380 days.

(21) Appl. No.: 18/153,313

(22) Filed: Jan. 11, 2023

(65) Prior Publication Data
US 2024/0122669 A1 Apr. 18, 2024

(30) Foreign Application Priority Data
Oct. 17, 2022 (TW) .................. 111139310

(51) Int. Cl.
*A61B 90/14* (2016.01)
*A61D 1/00* (2006.01)

(52) U.S. Cl.
CPC ............. *A61B 90/14* (2016.02); *A61D 1/00* (2013.01)

(58) Field of Classification Search
CPC ......... A61B 34/30; A61B 90/11; A61B 34/20; A61B 90/10; A61B 90/14; A61D 1/00; A61D 1/005; A61D 1/02; A61D 1/025; A61D 1/04; A61D 2003/003; A61D 15/00; A01K 1/0613; A01K 11/002; A01K 1/06

See application file for complete search history.

(56) References Cited

U.S. PATENT DOCUMENTS

| 6,080,164 A * | 6/2000 | Oshio ............... A61B 90/10 606/130 |
| 6,267,773 B1 * | 7/2001 | Gadberry .......... A61B 17/1227 606/151 |
| 2019/0239776 A1 * | 8/2019 | Dekel ................ A61B 5/1114 |

FOREIGN PATENT DOCUMENTS

CN 112274407 A * 1/2021

* cited by examiner

*Primary Examiner* — Katherine M Shi
(74) *Attorney, Agent, or Firm* — HSML P.C.

(57) ABSTRACT

An ear canal clamp for small animals includes a base and a clamping mechanism. The clamping mechanism includes two clamping arms movably mounted on the base, a biasing member mounted on the base and constrained between the clamping arms, and two ear canal positioning members mounted respectively to the clamping arms and facing each other. The clamping arms are configured to move toward each other and compress the biasing member to increase the distance between the ear canal positioning members. A biasing force generated by the biasing member when compressed is used to push the clamping arms to move oppositely with respect to each other.

10 Claims, 9 Drawing Sheets

EAR CANAL CLAMP FOR SMALL ANIMALS

CROSS-REFERENCE TO RELATED APPLICATION

This application claims priority to Taiwanese Invention Patent Application No. 111139310, filed on Oct. 17, 2022.

FIELD

The disclosure relates to an ear canal clamp, more particularly to an ear canal clamp for small animals.

BACKGROUND

A small animal stereotaxic instrument is a common research tool used in the neurological field to find specific positions in the brain structure of a small animal so that experiments may be performed. Stereotaxic surgery is conducted by stably mounting the small animal on the stereotaxic instrument by affixing the head of the animal from three points (e.g., both ears canals and the incisor teeth of a rodent) and establishing a three-dimensional coordinate system with respect to a reference point, which is generally the bregma on the skull of the small animal. The abovementioned stereotaxic instrument for small animals has been widely used, and is often employed in brain surgery, intracerebroventricular implant surgery, intracerebroventricular injection, and brain measurement. However, the correct placement of the small animal on the stereotaxic instrument relies heavily on user experience and technique which creates a high hurdle for inexperienced researchers to overcome. For researchers which are not drilled in the placement of small animals, their operating time in experiments may overrun and their errors in positioning may cause the experiments to fail.

SUMMARY

Therefore, an object of the disclosure is to provide an ear canal clamp that can alleviate at least one of the drawbacks of the prior art.

According to the disclosure, an ear canal clamp includes a base and a clamping mechanism.

The clamping mechanism includes two clamping arms movably mounted on the base, a biasing member mounted on the base and constrained between the clamping arms, and two ear canal positioning members mounted respectively to the clamping arms and facing each other. The clamping arms are configured to move toward each other and compress the biasing member to increase the distance between the ear canal positioning members. A biasing force generated by the biasing member when compressed is used to push the clamping arms to move oppositely with respect to each other.

BRIEF DESCRIPTION OF THE DRAWINGS

Other features and advantages of the disclosure will become apparent in the following detailed description of an embodiment with reference to the accompanying drawings. It is noted that various features may not be drawn to scale.

DETAILED DESCRIPTION

Figure 1:
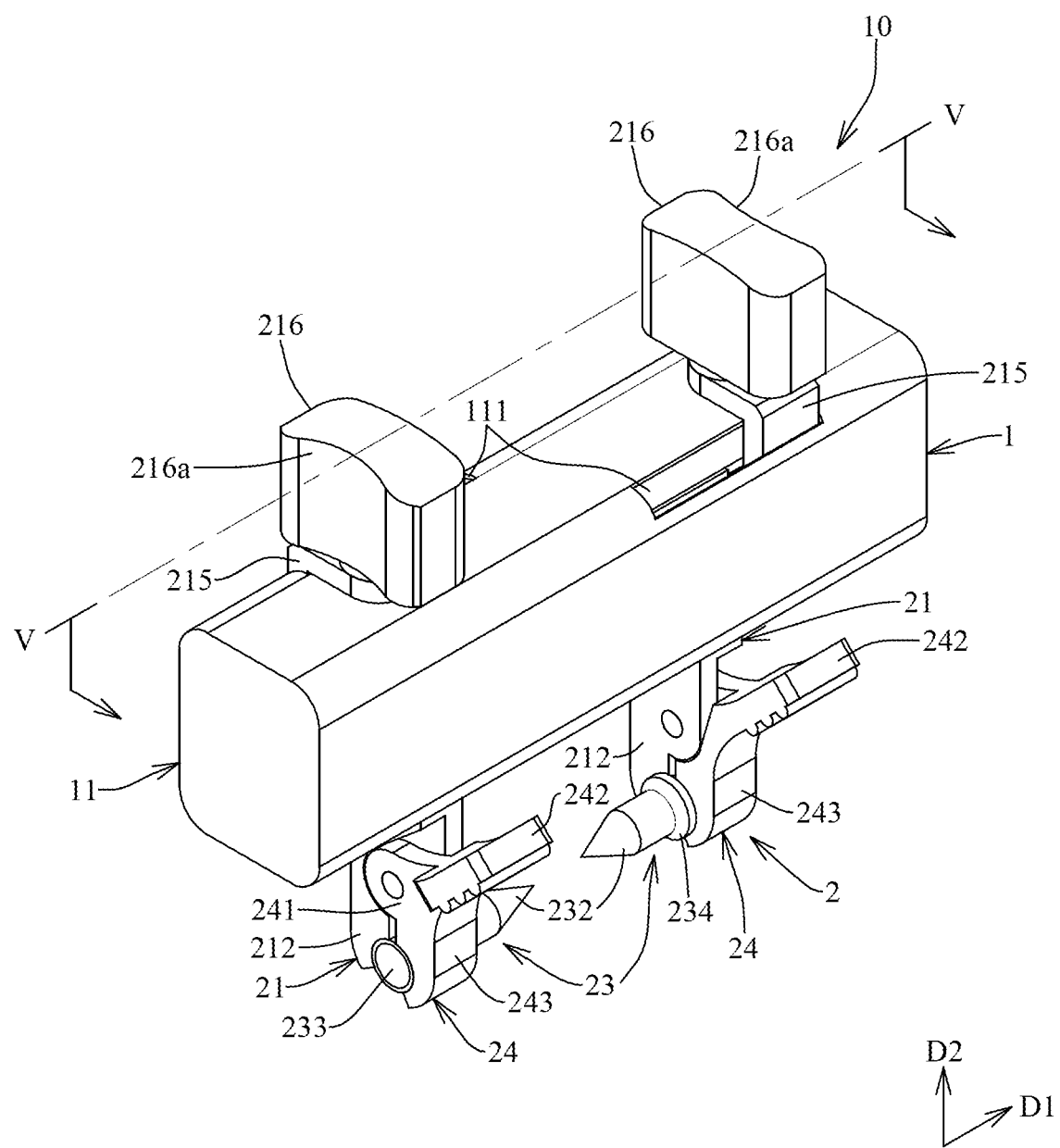
FIG. 1 is a perspective view illustrating the embodiment of an ear canal clamp according to the disclosure when two clamping arms are in an initial state.

Before the disclosure is described in greater detail, it should be noted that where considered appropriate, reference numerals or terminal portions of reference numerals have been repeated among the figures to indicate corresponding or analogous elements, which may optionally have similar characteristics.

Figure 2:
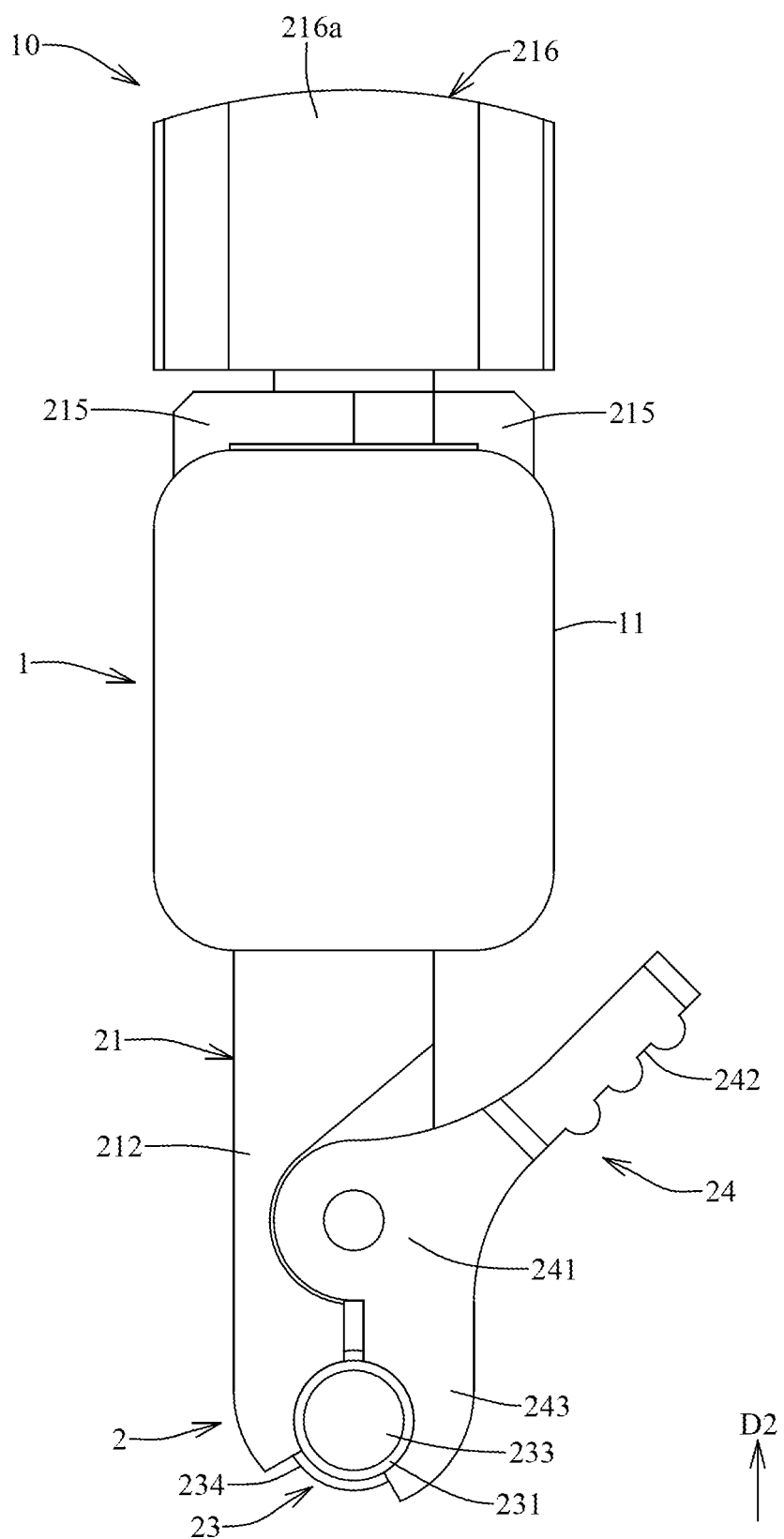
FIG. 2 is a schematic side view of the embodiment.

Referring to FIGS. 1 and 2, the embodiment of an ear canal clamp 10 of the disclosure can be used in conjunction with a small animal stereotaxic instrument (not shown) to position ear canals of a small animal, such as a rodent. The ear canal clamp 10 includes a base 1, and a clamping mechanism 2.

Figure 3:
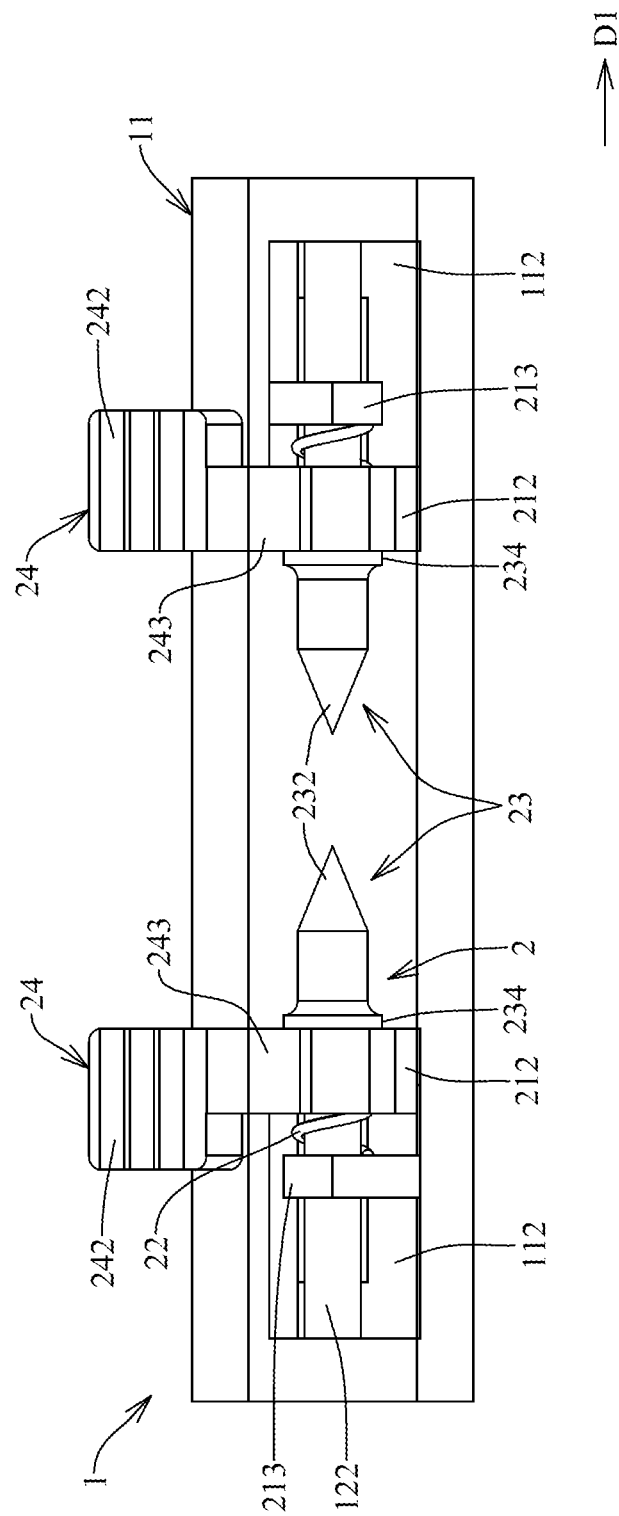
FIG. 3 is a schematic bottom view of the embodiment.
Figure 4:
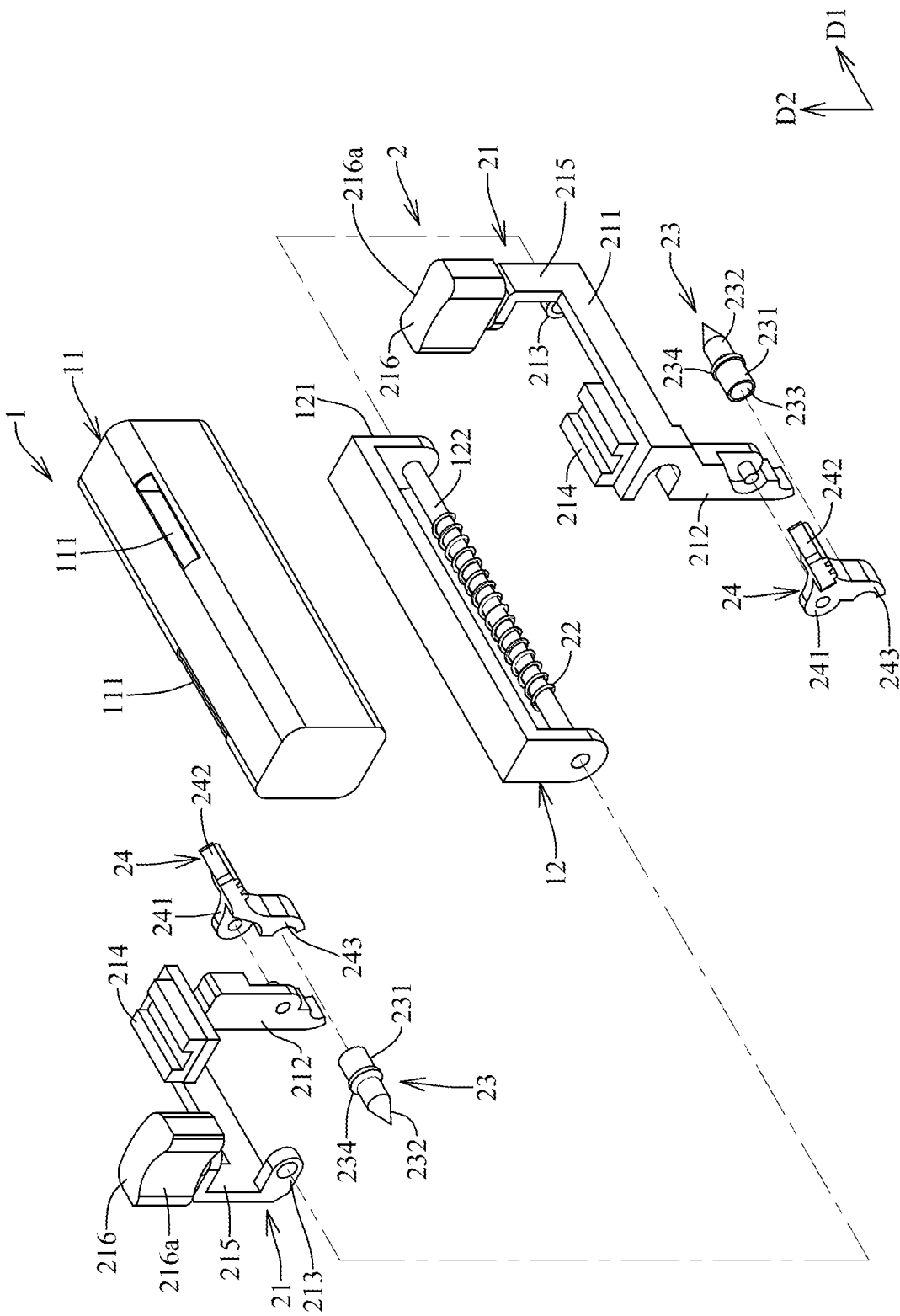
FIG. 4 is an exploded perspective view of the embodiment.
Figure 5:
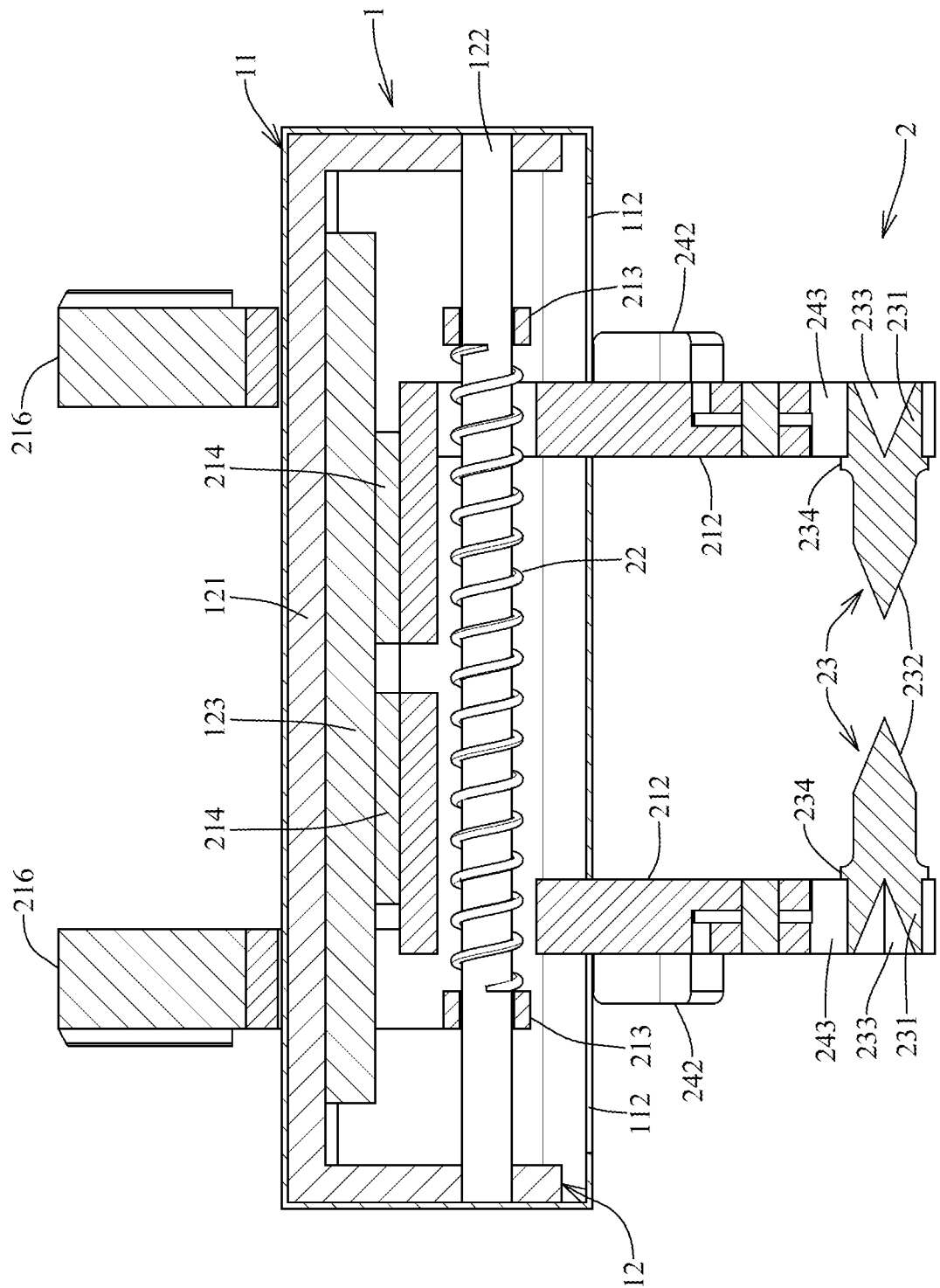
FIG. 5 is a schematic partially sectional view of the embodiment taken along line V-V of FIG. 1, where a guide rod and a biasing member are not shown in cross section.

Further referring to FIGS. 3 to 5, the base 1 includes a housing 11 extending in a transverse direction (D1) (e.g., left-right direction) and substantially cuboid, and a guide frame 12 disposed in the housing 11. The guide frame 12 includes a frame body 121 fixed to the housing 11 and generally inverted U-shaped, a guide rod 122 extending in the transverse direction (D1) through the frame body 121, and a guide rail 123 connected to the frame body 121, extending in the transverse direction (D1), and spaced apart from the guide rod 122 (see FIG. 5). In this embodiment, the housing 11 has a top surface that is formed with two upper limiting grooves 111 that are staggered and that are extending in the transverse direction (D1), and a bottom surface that is formed with two lower limiting grooves 112 symmetrical with respect to each other and extending in the transverse direction (D1). In this embodiment, the upper limiting grooves 111 are, for example, elongated slots (see FIG. 4), and the lower limiting grooves 112 are, for example, substantially rectangular openings (see FIG. 3).

Figure 6:
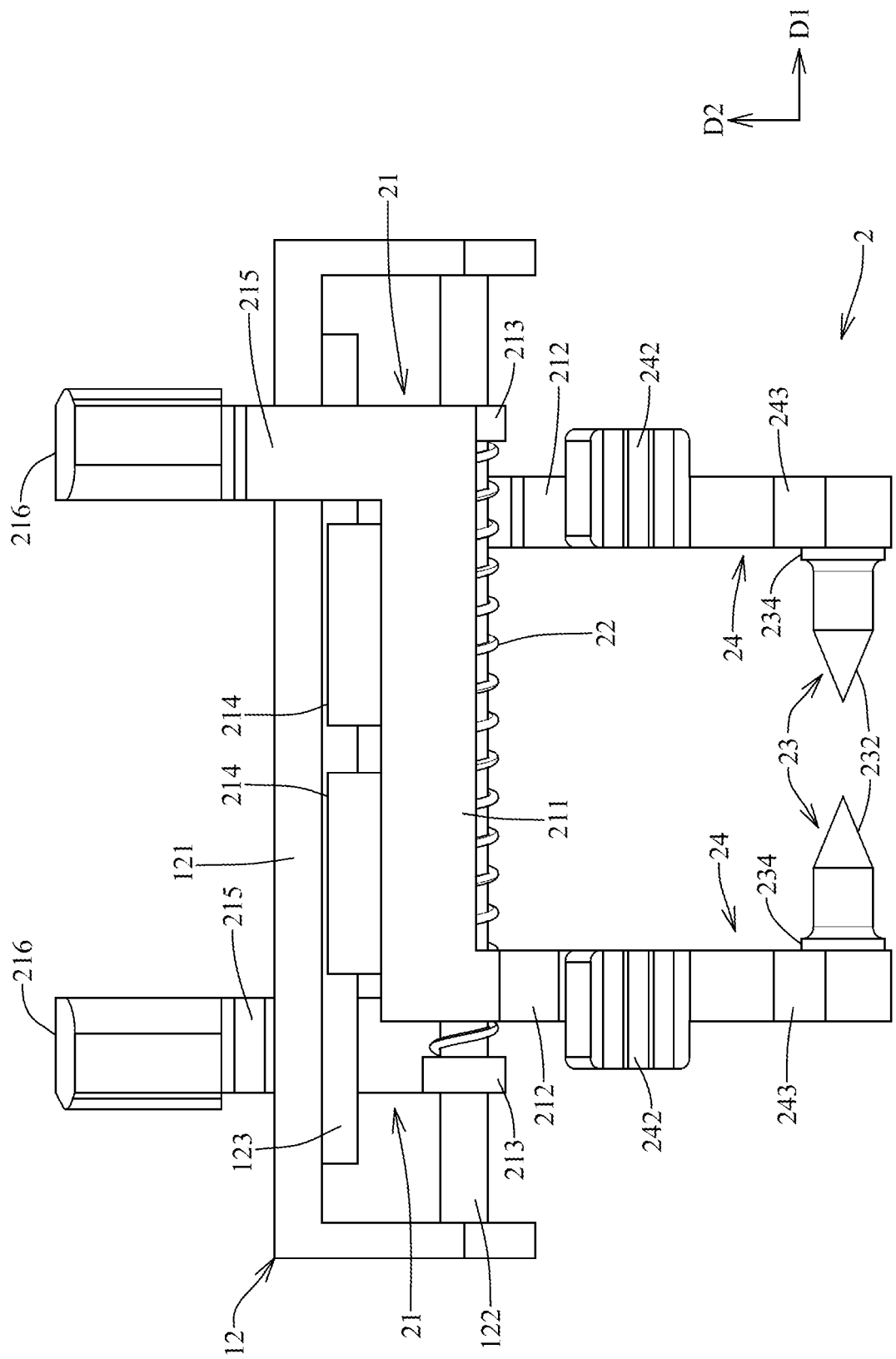
FIG. 6 is a schematic front view illustrating the embodiment without a housing when the clamping arms are in the initial state.

Referring to FIGS. 4 to 6, the clamping mechanism 2 includes two clamping arms 21, a biasing member 22, two ear canal positioning members 23, and two clamping members 24.

The clamping arms 21 are disposed movably on the base 1. In this embodiment, each clamping arm 21 has a slide arm portion 211, a mounting portion 212, a ring portion 213, a guide block portion 214, a linking portion 215, and an operating portion 216. The structure and effect of a single clamping arm 21 will be described in further detail below. The slide arm portion 211 extends in the transverse direction (D1), and has two end portions (i.e., left and right end portions) opposite to each other in the transverse direction (D1). The mounting portion 212 is connected to one of the end portions (e.g., left end portion) of the slide arm portion 211, and extends in a longitudinal direction (D2) (e.g., up-down direction) that is perpendicular to the transverse direction (D1) outwardly from the housing 11 through one of the lower limiting grooves 112 (e.g., lower limiting groove 112 on the left in FIG. 5) of the housing 11. The ring portion 213 is connected to the other one of the end portions (e.g., right end portion) of the slide arm portion 211, and is movably sleeved on the guide rod 122 of the guide frame 12. The guide block portion 214 is connected to the upper side of one of the end portions (e.g., left end portion) of the slide arm portion 211, and slidably engages the guide rail 123 of the guide frame 12. The linking portion 215 is connected to the other one of the end portions of the slide arm portion 211 (i.e., the right end portion distal from the mounting portion 212), and extends outwardly from the housing through a corresponding one of the upper limiting grooves 111 in the housing 11 so that the linking portion 215 is constrained to move in the corresponding one of the upper limiting grooves 111. The operating portion 216 is connected to the linking portion 215 and is exposed from the housing 11. In this embodiment, the operating portion 216 is, for example, block-shaped, and has a concave curved side surface (216a) adapted to be pressed by a user's finger and made of an anti-slip material. However, in other implementations, the side surface of the operating portion may also be a flat surface formed with a plurality of anti-slip textures. Alternatively, the operating portion 216 may have a ring structure adapted to be sleeved on a user's finger for operation.

The biasing member 22 is disposed on the guide rod 122 and is constrained between the clamping arms 21. In this embodiment, the biasing member 22 is, for example, a coil spring sleeved on the guide rod 122 of the guide frame 12, and has two ends (see FIG. 5) opposite to each other in the transverse direction (D1) and abutting respectively against the ring portions 213 of the clamping arms 21. When the clamping arms 21 are operated to move toward each other to compress the biasing member 22 (see FIG. 9), a biasing force generated by the biasing member 22 when compressed is used to push the clamping arms 21 to move oppositely with respect to each other so that the clamping arms 21 return to an initial state shown in FIGS. 1 and 5.

Figure 7:
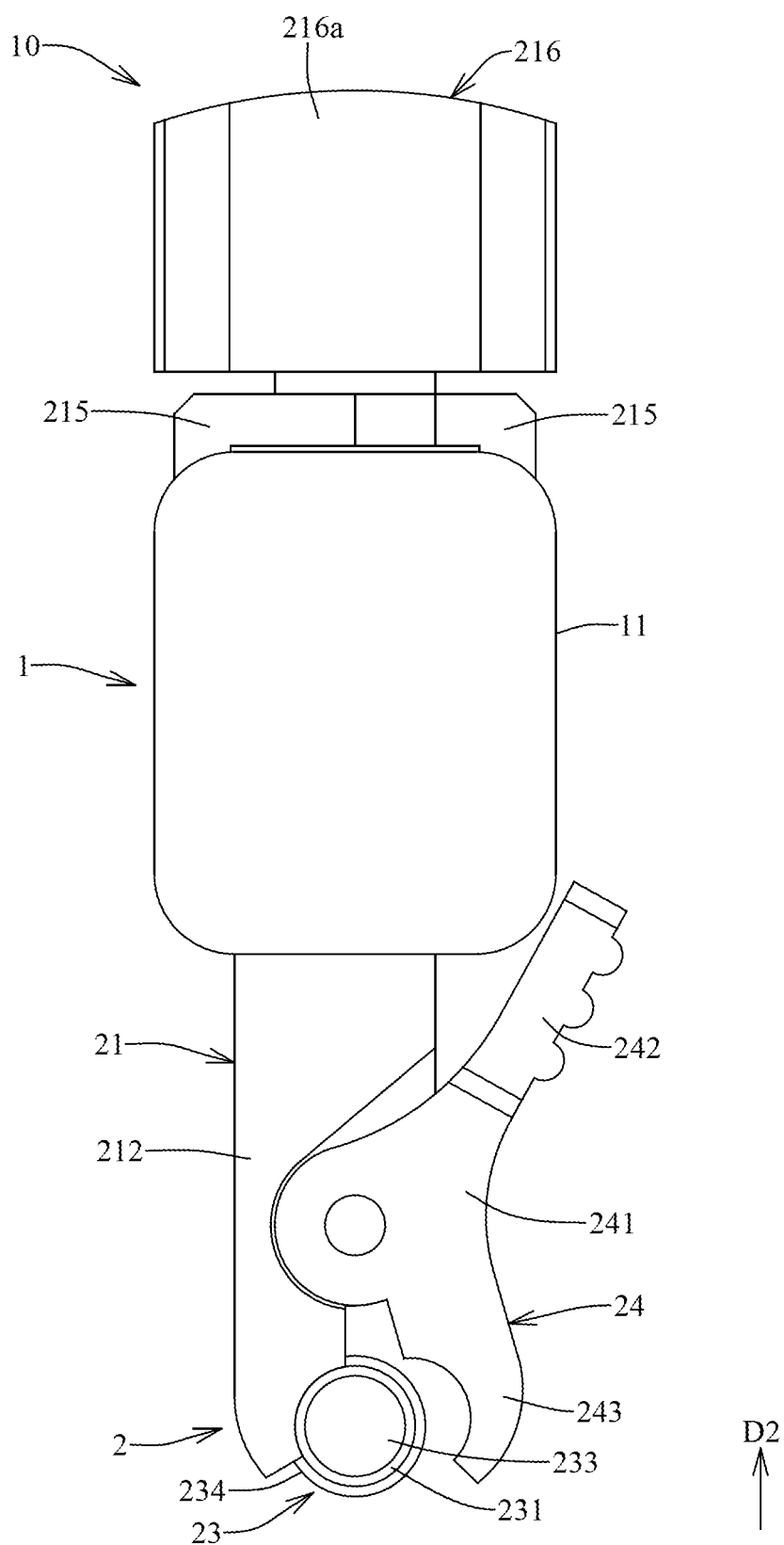
FIG. 7 is a schematic side view illustrating the embodiment when a clamping member of a clamping mechanism releases a corresponding ear canal positioning member.

Referring to FIGS. 2, 4 and 7, the clamping members 24 are connected respectively and pivotally to the mounting portions 212 of the clamping arms 21. In this embodiment, each clamping member 24 is configured to cooperate with the mounting portion 212 of a corresponding one of the clamping arms 21 to clamp a corresponding one of the ear canal positioning members 23 therebetween. Each clamping member 24 has a pivot portion 241, an operating end portion 242, and a clamping end portion 243. The structure and effect of a single clamping member 24 will be further described in detail below. The pivot portion 241 is connected pivotally to the mounting portion 212 of the corresponding one of the clamping arms 21, and is connected to the clamping end portion 243 and the operating end portion 242 so that the operating end portion 242 extends away from the mounting portion 212 of the corresponding one of the clamping arms 21 and that the clamping end portion 243 is proximate to the mounting portion 212 of the corresponding one of the clamping arms 21. More specifically, the clamping end portion 243 is configured to cooperate with the mounting portion 212 of the corresponding one of the clamping arms 21 to clamp the corresponding one of the ear canal positioning members 23 therebetween (see FIG. 2). In use, if it is desired to replace another ear canal positioning member 23, the operating end portion 242 is operable to move toward the mounting portion 212 of the corresponding one of the clamping arms 21 (i.e., the operating end portion 242 is pushed upwardly toward the mounting portion 212 of the corresponding one of the clamping arms 21) to move the clamping end portion 243 away from the mounting portion 212 of the corresponding one of the clamping arms 21 to release the corresponding one of the ear canal positioning members 23 (see FIG. 7). It is noted that, in this embodiment, a spring member (not shown), such as a torsion spring, is disposed between the operating end portion 242 and the mounting portion 212 of the corresponding one of the clamping arms 21. An elastic restoring force generated by the spring member when compressed is used to urge the operating end portion 242 to move away from the mounting portion 212 so that the clamping end portion 243 clamps the corresponding one of the ear canal positioning members 23. However, in other embodiments, a fastening member (not shown), such as a short screw bolt, can be threaded between the operating end portion 242 and the mounting portion 212 of the corresponding one of the clamping arms 21 to replace the aforesaid spring member. The fastening member is rotatable in a particular rotational direction to push the operating end portion 242 away from the mounting portion 212 of the corresponding one of the clamping arms 21 so that the clamping end portion 243 clamps the corresponding one of the ear canal positioning members 23.

It should be particularly noted that, in this embodiment, the mounting portion 212 of each clamping arm 21 cooperates with the corresponding one of the clamping members 24 to clamp the corresponding one of the ear canal positioning members 23 therebetween so that the ear canal positioning members 23 face each other in the transverse direction (D1) (see FIG. 1). However, in other embodiments, the clamping members 24 may also be omitted, as long as the mounting portion 212 of each clamping arm 21 is designed to have a structure that permits the corresponding one of the ear canal positioning members 23 to be detachably mounted thereto, such as a locking structure that releasably fastens the corresponding one of the ear canal positioning members 23 thereto.

In this embodiment, each ear canal positioning member 23 has a clamped end portion 231 formed with a positioning groove 233, a conical probe end portion 232 opposite to the clamped end portion 231, and an outer annular flange 234 disposed between the clamped end portion 231 and the probe end portion 232. For each ear canal positioning member 23, the probe end portion 232 is adapted to extend into an ear canal of a small animal, and the positioning groove 233 is, for example, a groove formed in an end surface of the clamped end portion 231 and permits a component of the small animal stereotaxic instrument (e.g., a positioning ear bar) to be inserted thereinto. More specifically, during installation, the mounting portion 212 of each clamping arm 21 cooperates with the clamping end portion 243 of the corresponding one of the clamping members 24 to clamp the clamped end portion 231 of the corresponding one of the ear canal positioning members 23 so that the outer annular flange 234 of the corresponding one of the ear canal positioning members 23 abuts against the mounting portion 212 of the clamping arm 21 and the clamping end portion 243 (see FIG. 3) of the corresponding one of the clamping member 24 to ensure proper positioning of the probe end portion 232 and that the probe end portions 232 of the ear canal positioning members 23 face each other. It is important to note that the outer annular flange 234 of each ear canal positioning member 23 can be considered a foolproof mechanism which can ensure that each ear canal positioning member 23 is correctly positioned on a corresponding one of the clamping arms 21, thereby effectively avoiding improper installation.

Figure 8:
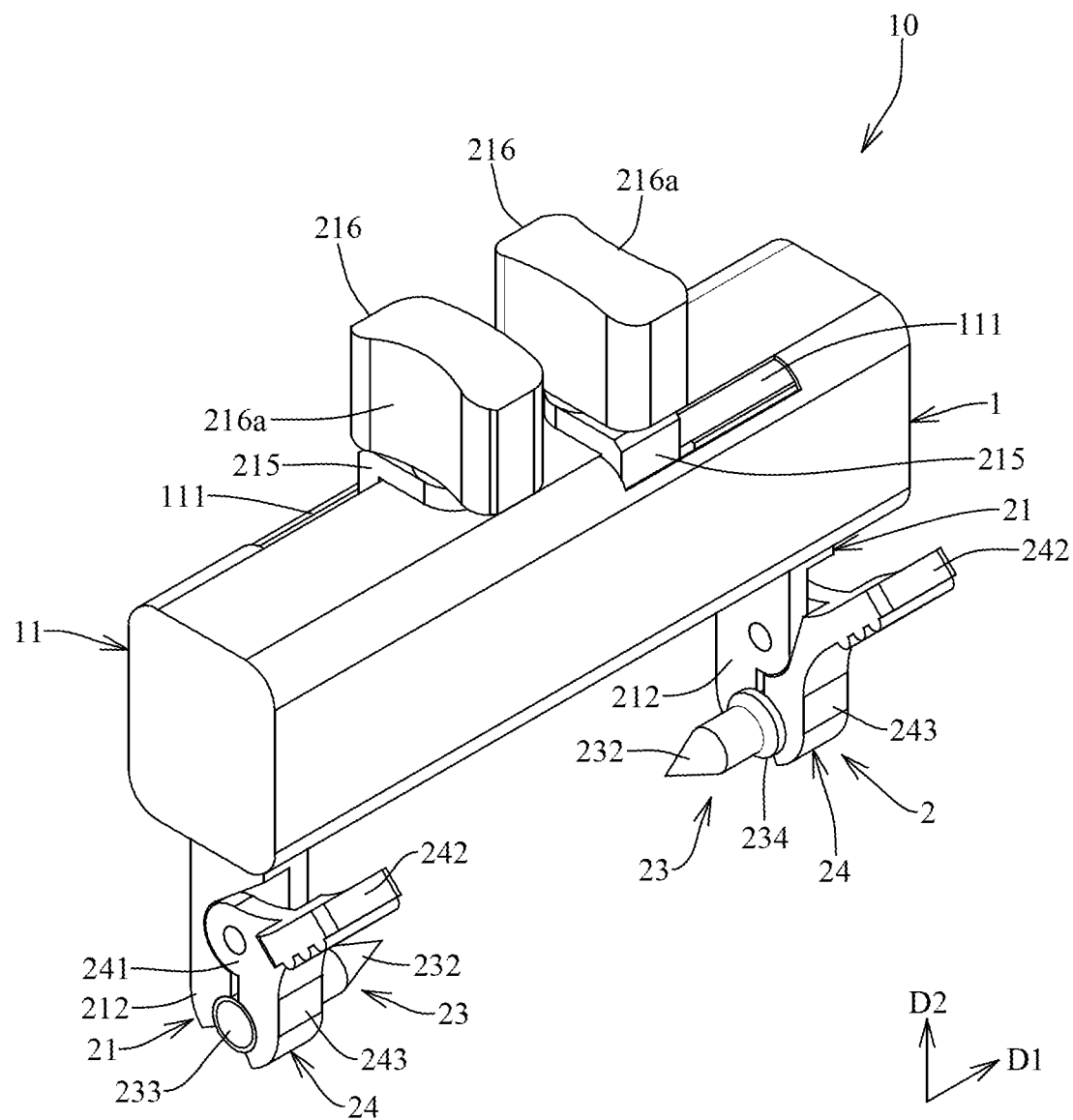
FIG. 8 is a perspective view illustrating the embodiment when the clamping arms are in an open state.
Figure 9:
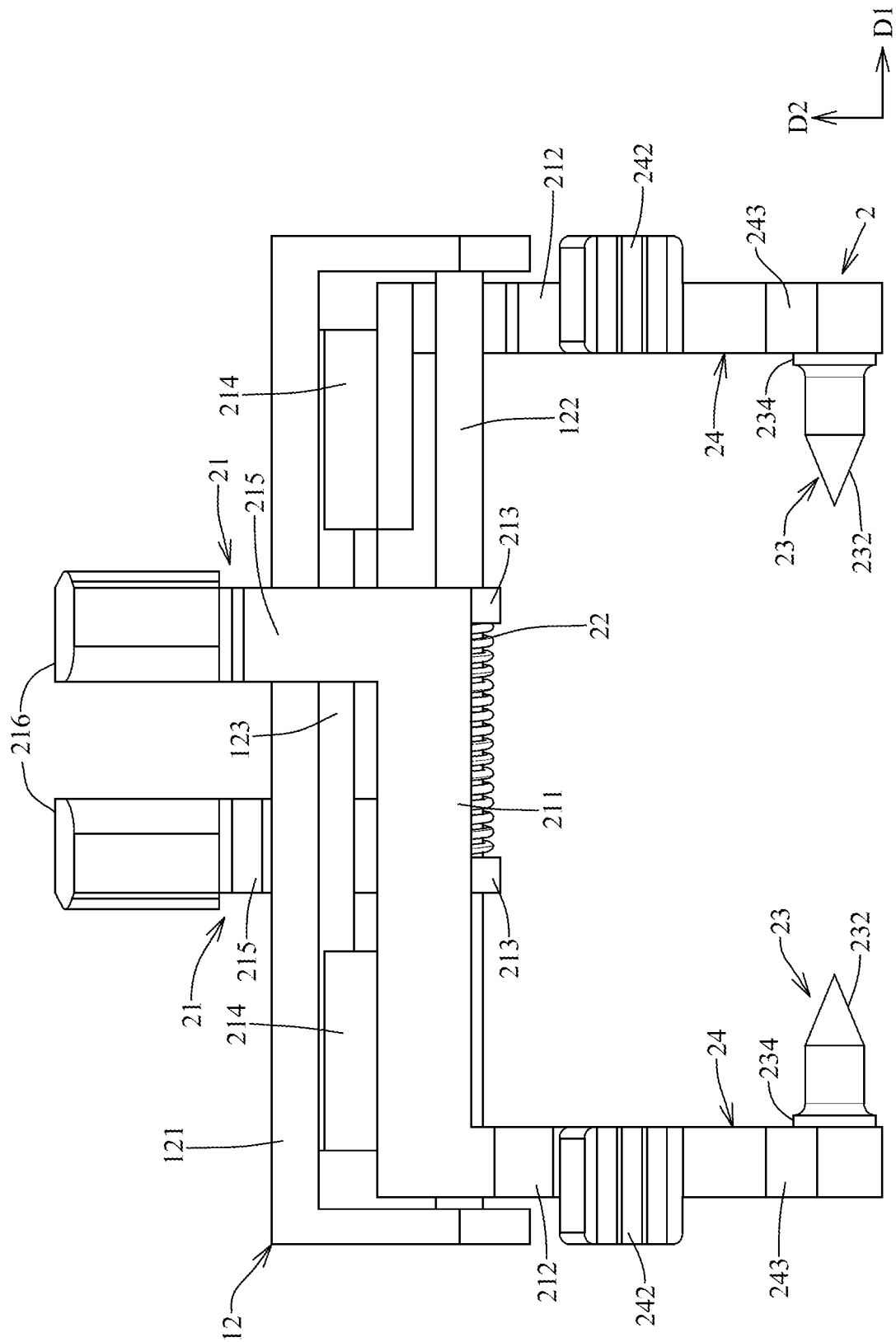
FIG. 9 is a schematic front view illustrating the embodiment without the housing when the clamping arms are in the open state.

Referring to FIGS. 5, 8 and 9, the clamping arms 21 can be operated in the initial state (see FIG. 1) and an open state (see FIG. 8). When the clamping arms 21 are in the initial state, the biasing member 22 is not compressed. By manual operation, for example, pressing the operating portions 216 of the clamping arms 21 respectively by two fingers of a user, the clamping arms 21 are moved toward each other to compress the biasing member 22 and increase the distance between the ear canal positioning members 23 so that the clamping arms 21 are in the open state. Once the fingers release the operating portions 216, a biasing force generated by the biasing member 22 will push the clamping arms 21 to move oppositely with respect to each other so that the clamping arms 21 return to the initial state.

In order to correctly dispose a small animal on the small animal stereotaxic instrument, the ear canal clamp 10 of the disclosure can be used as an auxiliary positioning device. An auxiliary positioning procedure for two ear canals of the small animal using the ear canal clamp 10 includes the steps of: (i) first manually operating the clamping arms 21 to the open state; (ii) placing the head of the small animal between the probe end portions 232 of the ear canal positioning members 23; (iii) releasing the operating portions 216 of the clamping arms 21 such that the head of the small animal is clamped by the clamping arms 21 moving toward each other and that the probe end portions 232 of the ear canal positioning members 23 are inserted respectively into the ear canals of the small animal, thereby accurately positioning the ear canals of the small animal, at which time the biasing force generated by the biasing member 22 prevents the ear canal positioning members 23 from slipping off the ear canals of the small animal; (iv) placing the head of the small animal together with the ear canal clamp 10 on the small animal stereotaxic instrument so that two positioning ear bars respectively disposed on opposite sides of the small animal stereotaxic instrument are respectively inserted into the positioning grooves 233 of the ear canal positioning members 23, thereby completing the positioning of the positioning ear bars of the small animal stereotaxic instrument; and (v) manually operating the clamping members 24 to release the ear canal positioning members 23. Thus, the small animal is correctly positioned on the small animal stereotaxic instrument.

However, in other embodiments, each ear canal positioning member can also be connected integrally to the mounting portion 212 of the corresponding one of the clamping arms 21 (not shown), and the clamping members 24 can thus be omitted.

In summary, through operation of the clamping arms 21, the distance between the probe end portions 232 of the ear canal positioning members 23 is increased, which is advantageous for probing the ear canals of small animals. After the probe end portions 232 of the ear canal positioning members 23 are inserted respectively into the ear canals of the small animal, the biasing force generated by the biasing member 22 can urge the clamping arms 21 to move in opposite directions to provide appropriate pressure to avoid the ear canal positioning members 23 falling out of the ear canals of the small animal. The ear canal clamp 10 of this disclosure can be operated through one-handed operation of the clamping arms 21 and the clamping members 24, and can indeed significantly reduce the difficulties, and time spent during the positioning of the ear canals using the small animal stereotaxic instrument, thereby preventing positioning errors. Therefore, the ear canal clamp according to the present disclosure achieves the effects of simple operation and rapid and accurate ear canal positioning.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An ear canal clamp comprising:
   a base; and
   a clamping mechanism including two clamping arms movably mounted on the base, a biasing member mounted on the base and constrained between said clamping arms, and two ear canal positioning members mounted respectively to said clamping arms and facing each other, said clamping arms being configured to move toward each other and compress said biasing member to increase a distance between said ear canal positioning members, a biasing force generated by said biasing member when compressed being used to push said clamping arms to move oppositely with respect to each other.

2. The ear canal clamp as claimed in claim 1, wherein:
   each of said clamping arms includes a slide arm portion extending in a transverse direction, and a mounting portion connected to one end portion of said slide arm portion and extending in a longitudinal direction; and
   said clamping mechanism further includes two clamping members respectively pivoted to said mounting portions of said clamping arms, each of said clamping members being configured to cooperate with said mounting portion of a corresponding one of said clamping arms to clamp a corresponding one of said ear canal positioning members therebetween.

3. The ear canal clamp as claimed in claim 2, wherein each of said clamping members includes:
   a pivot portion connected pivotally to said mounting portions of the corresponding one of said clamping arms, an operating end portion connected to said pivot portion and extending away from said mounting portion of the corresponding one of said clamping arms, and a clamping end portion connected to the pivot portion and proximate to said mounting portion of the corresponding one of said clamping arms, wherein said clamping end portion of each of said clamping members being configured to cooperate with said mounting portion of the corresponding one of said clamping arms to clamp the corresponding one of said ear canal positioning members therebetween, said operating end portion of each of said clamping members being operable to move toward said mounting portion of the corresponding one of said clamping arms so that said clamping end portion of each of said clamping members moves away from said mounting portion of the corresponding one of said clamping arms to release the corresponding one of said ear canal positioning members.

4. The ear canal clamp as claimed in claim 2, wherein:

said base includes a housing, and a guide frame disposed in said housing, said guide frame including a guide rod extending in the transverse direction;

each of said clamping arms further includes a ring portion connected to said slide arm portion thereof and movably sleeved on said guide rod of said guide frame; and said biasing member is mounted on said guide rod, and includes two ends opposite to each other in the transverse direction and abutting respectively against said ring portions of said clamping arms.

5. The ear canal clamp as claimed in claim 4, wherein:
said guide frame further includes a frame body fixed on said base and permitting said guide rod to extend therethrough, and a guide rail connected to said frame body, extending in the transverse direction and spaced apart from said guide rod; and each of said clamping arms further includes a guide block portion connected to said slide arm portion and slidably engaging said guide rail.

6. The ear canal clamp as claimed in claim 5, wherein:

said housing is formed with two upper limiting grooves extending in the transverse direction (D1); and each of said clamping arms further includes a linking portion that is connected to the other end of the slide arm portion distal from said mounting portion and that extends outwardly from said housing through a corresponding one of said upper limiting grooves, and an operating portion connected to said linking portion and exposed from said housing, said linking portion of each of said clamping arms being confined to move in the corresponding one of said upper limiting grooves.

7. The ear canal clamp as claimed in claim 6, wherein said operating portion of each of said clamping arms is block-shaped, and has a concave curved side surface adapted to be pressed by a user's finger.

8. The ear canal clamp as claimed in claim 6, wherein said operating portion of each of said clamping arms is made of an anti-slip material.

9. The ear canal clamp as claimed in claim 2, wherein:

each of said ear canal positioning members includes a clamped end portion formed with a positioning groove, and a probe end portion opposite to said clamped end portion; and said clamping end portion of each of said clamping members, and said mounting portion of the corresponding one of said clamping arms cooperatively clamp said clamped end portion of the corresponding one of said ear canal positioning members therebetween so that said probe end portions of said ear canal positioning members face each other in the transverse direction.

10. The ear canal clamp as claimed in claim 9, wherein each of said ear canal positioning members further includes an outer annular flange that is disposed between said clamped end portion and said probe end portion and that abuts against said mounting portion of a corresponding one of said clamping arms and a corresponding one of said clamping members.

* * * * *

UNITED STATES PATENT AND TRADEMARK OFFICE
CERTIFICATE OF CORRECTION

| | | |
|---|---|---|
| PATENT NO. | : 12,336,863 B2 | Page 1 of 1 |
| APPLICATION NO. | : 18/153313 | |
| DATED | : June 24, 2025 | |
| INVENTOR(S) | : Peng et al. | |

It is certified that error appears in the above-identified patent and that said Letters Patent is hereby corrected as shown below:

On the Title Page

(73) After Assignee: Delete: "LEGO STONE CO., LTD., Taichung (TW)" and insert --TAIPEI MEDICAL UNIVERSITY, Taipei (TW)--.

Signed and Sealed this
Thirtieth Day of September, 2025

John A. Squires
*Director of the United States Patent and Trademark Office*